United States Patent [19]

Ersfeld et al.

[11] Patent Number: 4,683,877

[45] Date of Patent: Aug. 4, 1987

[54] ORTHOPEDIC CASTING ARTICLE AND METHOD

[75] Inventors: Dean A. Ersfeld, Maplewood, Minn.; Timothy C. Sandvig, Woodville, Wis.; Diane S. Gobran, Roseville, Minn.

[73] Assignee: Minnesota Mining and Manufacturing Company, St. Paul, Minn.

[21] Appl. No.: 784,345

[22] Filed: Oct. 4, 1985

[51] Int. Cl.⁴ ................................................ A61F 5/04
[52] U.S. Cl. ..................................... 128/90; 428/230; 428/251; 428/253; 428/308.4; 428/317.3; 428/317.7; 428/423.3; 428/425.6; 428/913
[58] Field of Search ................. 128/90; 428/230, 253, 428/308.4, 317.3, 317.7, 423.3, 425.6, 251, 913

[56] References Cited

U.S. PATENT DOCUMENTS

| | | | |
|---|---|---|---|
| 2,759,475 | 8/1956 | Van Swaay | 128/90 |
| 2,800,129 | 7/1957 | Van Swaay | 128/90 |
| 3,040,740 | 6/1962 | Parker | 128/83 |
| 3,048,169 | 8/1962 | Pierce | 128/90 |
| 3,301,252 | 1/1967 | Mahoney, Jr. | 128/90 |
| 3,373,741 | 3/1968 | Hill et al. | 128/90 |
| 3,375,822 | 4/1968 | Rose | 128/90 |
| 3,572,330 | 3/1971 | Gander | 128/90 |
| 3,656,475 | 4/1972 | Hanrahan | 128/90 |
| 3,728,206 | 4/1973 | Buese | 161/112 |
| 3,819,796 | 6/1974 | Webster et al. | 264/321 |
| 3,935,355 | 1/1976 | Kuhn | 128/90 |
| 3,998,219 | 12/1976 | Mercer et al. | 128/89 |
| 4,019,506 | 4/1977 | Eschmann | 128/90 |
| 4,060,075 | 11/1977 | Blomer et al. | 128/90 |
| 4,193,395 | 3/1980 | Gruber | 128/90 |
| 4,309,990 | 1/1982 | Brooks et al. | 128/90 |
| 4,323,061 | 4/1982 | Usukura | 128/90 |
| 4,331,134 | 5/1982 | Brooks et al. | 128/90 |
| 4,376,438 | 3/1983 | Straube et al. | 128/90 |
| 4,411,262 | 10/1983 | von Bonin et al. | 128/90 |
| 4,433,680 | 2/1984 | Yoon | 128/90 |
| 4,442,833 | 4/1984 | Dahlen et al. | 128/90 |
| 4,450,833 | 5/1984 | Brooks et al. | 128/90 |
| 4,451,310 | 5/1984 | Lairloup | 156/78 |
| 4,502,479 | 3/1985 | Garwood et al. | 128/90 |

FOREIGN PATENT DOCUMENTS

WO83/01736  5/1983  PCT Int'l Appl. .

*Primary Examiner*—James C. Cannon
*Attorney, Agent, or Firm*—Donald M. Sell; James A. Smith; Robert W. Hoke, II

[57] ABSTRACT

A casting article and method for forming an orthopedic cast around an animal body part. The article comprises a unitary blank having first and second lateral free edges. The blank is dimensioned and the free edges are shaped to extend the length of the body part and to at least circumferentially envelop the body part. The blank includes a pliant, extensible layer of a foam member, an extensible fabric bonded to the foam member and a curable resin which, upon activation of the resin and closure of the lateral free edges of the blank around the body part, results in the orthopedic cast.

35 Claims, 8 Drawing Figures

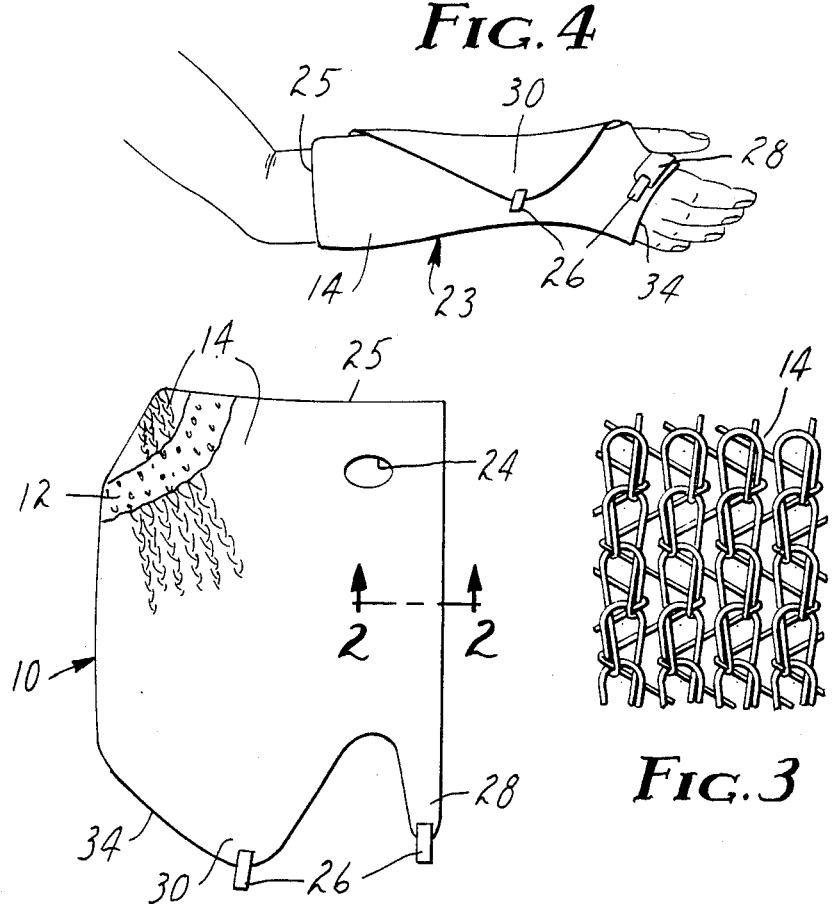

4,683,877

ORTHOPEDIC CASTING ARTICLE AND METHOD

FIELD OF THE INVENTION

This invention relates to the field of orthopedic casts. More particularly, it relates to orthopedic casting articles comprised of extensible blanks which are coated or impregnated with a curable resin.

BACKGROUND ART

Orthopedic casts are typically made by stationarily positioning the body part to be immobilized and circumferentially wrapping a length of pliant, hardenable tape in both lateral and circumferential overlapping relationship around the body part until sufficient wraps have been made to provide a cast which extends the length of the body part to be immobilized and has sufficient cross-sectional dimension to provide the necessary strength, rigidity, and durability to meet the demands recognized as necessary for orthopedic casts.

Many synthetic orthopedic casting tapes currently used comprise a fabric bandage, usually fiberglass, which is impregnated with a liquid resin which hardens upon exposure to moisture. Such casting bandages are described, for example, in U.S. Pat. Nos. 4,502,479, 4,433,680 and 4,376,438. Such casting bandages are typically provided in rolls of tape two to five inches (5.08 to 12.7 cm) wide, which are wrapped around the injured body member prior to hardening. Generally, multiple layers of the bandage are required to achieve the desired strength and rigidity. Since the bandage is often wrapped around body contours such as heels, elbows, etc., it is often necessary to make tucks or folds in the bandage, and a high level of skill is required in cast application in order to achieve a uniform, well-fitting cast. This problem has been somewhat alleviated by the introduction of highly extensible knit fabrics such as those used in "Scotchcast 2" casting materials available from 3M and described in copending application Ser. No. 668,881, filed Nov. 6, 1984 and assigned to the same assignee as the present invention. Such extensible fabric bandages can be more easily applied and will conform to body contours without the need for tucking and folding. However, the application must still be accomplished by a winding and wrapping process involving a plurality of overlapping layers.

In addition to tape bandages, a number of orthopedic casting systems more adapted to particular body parts have been devised. For example, U.S. Pat. Nos. 2,759,475 and 2,800,129 show blanks for forming splints comprising a solid thermoplastic material provided on one surface with a foam plastic layer. The blank is heated to a temperature such that the solid thermoplastic material becomes soft, and is then applied to the body part and shaped to form the splint. Similarly, U.S. Pat. No. 4,442,833 shows a casting or splinting bandage comprising a closed-cell polymer foam and a plurality of sheets of a textile material impregnated with a water curable resin. All three of these systems are described as further utilizing tapes, bandages or the like to aid the more shaped portion of the system in supporting the body part.

Apart from systems utilizing some form of tape, there are a number of casting systems utilizing reactive foams which are in situ hardened to form a closed cell foam around the body part. It is believed that those systems are generally difficult to handle, require a propellent, or come in a two part system requiring mixing. Hence, these systems are believed to be inconvenient to use, require a relatively high level of skill to apply and result in an occlusive cast construction that may promote patient skin masceration.

SUMMARY OF THE INVENTION

The present invention provides an article which greatly simplifies cast application and eliminates the need for applying overlapping wraps of a bandaging-type material. According to the invention, there is provided a casting article suitable for forming an orthopedic cast. The article comprises a unitary blank having first and second lateral free edges. The blank is dimensioned in one direction sufficient to extend the length of the body part and dimensioned in a second direction sufficient to at least circumferentially envelop the body part. The blank comprises a pliant, extensible layer of a foam member, an extensible fabric bonded to at least one major surface of the foam member, and a curable resin impregnatably associated with the blank. Upon activating the resin, laterally disposed portions of the blank can be stretched together into sealing relationship around the body part to provide the orthopedic cast. In a preferred embodiment, the resin is a moisture-curable, isocyanate-functional, polyurethane prepolymer including a tack-reducing agent, the fabric is a knitted fiberglass, the foam member is open celled, the resin is impregnating the foam member, and at least one of the lateral free edges of the blank has a curvilinear shape defining projection means which, in turn, aid in substantially eliminating wrinkles and puckers in the resultant cast.

Also according to the invention, there is provided a method of forming an orthopedic cast from the previously described article. The method includes activating the resin and stretching the blank around the body part. The method preferrably includes overlapping the blank upon itself to provide a double thickness over a predetermined portion of the body part.

BRIEF DESCRIPTION OF THE DRAWING

Other advantages of the invention will become apparent from the following drawing wherein like numerals refer to like parts.

FIG. 1 is a plan view of a preferred forearm embodiment of the orthopedic casting article of the present invention with portions broken away.

FIG. 2 is an enlarged cross-sectional view of the orthopedic casting article of FIG. 1 taken approximately along the line 2—2 of FIG. 1 with portions broken away.

FIG. 3 is an enlarged plan view of a portion of a preferred fiberglass fabric comprising the orthopedic casting article of FIG. 1.

FIG. 4 is a plan view of the orthopedic casting article of FIG. 1 formed into a forearm cast.

DETAILED DESCRIPTION

Figure 5:
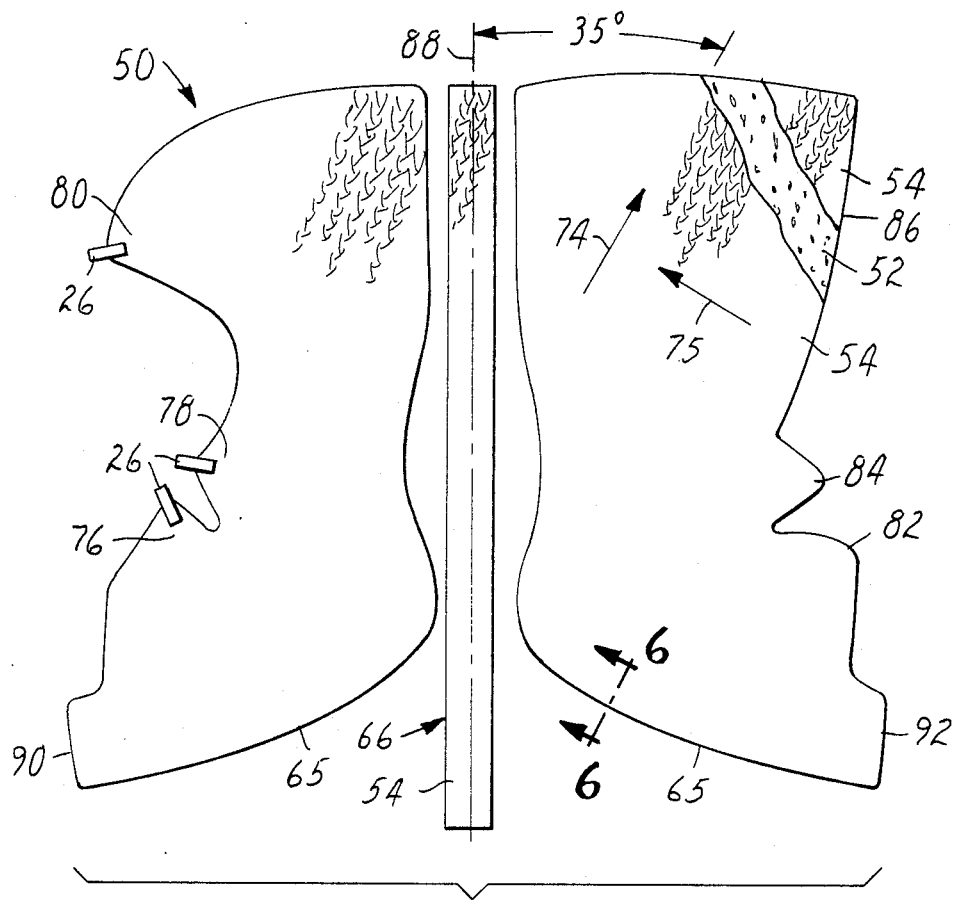
FIG. 5 is a partially fabricated, plan view of a preferred lower leg embodiment of the orthopedic casting article of the present invention with portions broken away.

Referring to the figures of the drawing wherein like numbers refer to like parts and in particular to FIG. 1, there is shown in plan view a preferred forearm orthopedic casting article 10 of the present invention in the form of a unitary blank with portions broken away. The article or blank 10 is generally comprised of a pliant, extensible layer or sheet of a foam member 12 which is preferably at least partially open-celled and backed on one side and preferably on both sides by an extensible fabric 14. A curable resin is impregnatably associated with the blank 10. Preferably, the foam member 12 and the fabric 14 are impregnated with the resin. The term "impregnated" is used to describe the condition in which the resin is thoroughly intermingled with and in surrounding relation to the fibers of the fabric 14 as well as to the wall membranes of the cells and the interconnected cell frame members of the foam member 12. The term "at least partially open-celled" is used to describe a foraminous structure having interconnecting or communicating orifices or cavities therein caused by a sufficient number of the wall membranes of the foam cells having been removed to allow impregnation of the foam member 12 with an effective amount of the resin so that an efficacious cast can subsequently be formed. The foam member 12 and the fabric 14 are bonded together to form the orthopedic casting article 10 having an overall, predetermined extensibility. Such bonding can be accomplished by conventional means such as by the use of adhesives, stitch bonding or by flame bonding. Flame bonding of the foam member 12 to the fabric 14 throughout their interface is preferred because of the continuous nature of the bond that is formed.

The foam member 12 can comprise any of a number of extensible foams which including those are at least partially open-celled such as polyester and polyether urethane foams where the cell sizes range from about 50–200 pores per linear inch (20–80 pores per linear centimeter). The number of pores per linear dimension is determined by measuring the diameter of the openings as defined by the interconnected cell frame members and by calculating the number of such openings that will fit into a linear dimension in a single plane. The foam member 12 is preferably $\frac{1}{8}$ inch (0.317 cm) thick polyurethane foam which is available from Illbruck U.S.A., Minneapolis, Minn. as type P-100 or E-150. It has been found that these foams, when impregnated with the preferred resin, will provide a cast of sufficient strength and air permeability to be efficacious.

The curable resin which is utilized in the cast article of this invention is preferably comprised of a moisture-curable, isocyanate-functional, polyurethane prepolymer as described in U.S. Pat. Nos. 4,502,479, 4,433,680 or 4,376,438. It is preferred to make this curable resin less tacky in accordance with the invention described in commonly assigned U.S. application Ser. No. 784,671, entitled Curable Resin Coated Sheet Having Reduced Tack, filed in the name of Matthew T. Scholz, et al. of even date herewith, now U.S. Pat. No. 4,667,661, and incorporated herein by reference. Reduced tackiness is achieved by a number of means as described in said U.S. patent application Ser. No., the result being that the kinetic coefficient of friction of the surface of the article 10 covered with resin-impregnated fabric member 14 is less than about 1.2. One technique for achieving such tack reduction is to lightly spray the surfaces of the resin-impregnated article 10 with a mixture of a polydimethylsiloxane, having a viscosity of at least 100 centistokes, and polyethylene oxide-long chain aliphatic hydrocarbon waxes. Alternately, a small amount of a polyethylene oxide-polypropylene oxide block copolymer may be added to the polyol during prepolymer preparation, after which the polydimethylsiloxane is sprayed onto the surface of the article 10 as before. The polydimethylsiloxane reduces resin tackiness prior to contact with water. The hydrophilic polyethylene oxide materials provide additional tack reduction upon contact with water. It is desirable to reduce resin tack to facilitate application of the article 10 to a patient's limb.

The fabric 14 which is utilized in the cast article of this invention can comprise a number of extensible fabrics including polyester and fiberglass fabrics. In order to obtain the preferred resin-impregnated, orthopedic casting article 10 of the present invention, it is necessary to start with a knitted fiberglass fabric which exhibits at least 40 percent extensibility in at least one direction. Preferably, the fabric exhibits at least 65 percent extensibility and most preferably at least 80 percent extensibility in one direction, e.g., the weft direction. The weft direction is the direction that is generally perpendicular to the machine or chain stitch direction, in the plane of the fabric. To determine extensibility within the context of the present invention, the following method was employed. A 4-inch by 4-inch (10.2 cm by 10.2 cm) piece of fabric is placed in the 1½ inch (3.81 cm) wide grips of a Model 1122 Instron Tensile Tester equipped with a 50 pound (22.7 Kg) load cell and set for a crosshead speed of 2 inches (5.08 cm) per minute and a chart speed of 2 inches (5.08 cm) per minute, and a load of 2 pounds (0.909 kg) is applied. The distance the chart moves to reach the load of 2 pounds (0.909 Kg) is the elongation of the fabric by this load in the direction according to the orientation of the fabric in the grips. A load of 2 pounds (0.909 Kg) is selected to approximate the maximum tension believed to be employed when applying the article 10.

The preferred knitted fiberglass fabrics are known. The preferred fabric 14 is shown in FIG. 3 to be a two bar, Raschel knit of 18 gauge to 36 gauge, knitted from a continuous filament fiberglass yarn called ECDE or ECC 37 1/0 to 75 1/0 available from PPG Industries, Inc., Pittsburgh, Penn. One yarn is used per guide needle. Bar 1 executes an open chain stitch while bar 2 inlays under two needles. This fabric is porous enough to allow water penetration into the article 10 and air circulation through the article 10. Two and three bar Raschel knits can be produced by regulating the amount of yarn in each stitch.

In addition to the initial extensibility described above, the knitted fabrics are preferably smooth and of a suitable thickness and porosity to insure good penetration of water, the curing agent, into the orthopedic casting article 10 and to provide a finished cast of sufficient strength and porosity. The importance of such fabric parameters are well known to those skilled in the art and are described, for example, in U.S. Pat. No. 4,502,479.

Referring now to FIG. 2, the orthopedic casting article 10 of FIG. 1 is shown in an enlarged cross-sectional view taken approximately along the line 2—2 of FIG. 1 with portions broken away. The foam member 12 comprises two major, opposite side surfaces 16 and 18 and a peripherally extending interconnecting edge surface 20. The side surfaces 16 and 18 are covered by or faced with the preferred fiberglass fabric 14. The preferred fabric and foam composite exhibits at least 12½ percent extensibility in at least one direction when tested by the method described earlier. The fabric 14 preferably extends to the edge surface 20 to envelop and thereby completely hide or contain the foam member 12 within the fabric 14. A seam 22 can be formed by conventionally stitching or heat or ultrasonically bonding but is preferably formed by heating the foam member 12 adjacent the edge surface 20 until the foam member 12 melts or is sufficiently softened to be compressed by conventional means to taper the two pieces of the fabric 14 together to provide the article 10 with a periphery that will result in a smooth, ridge-free cast. Alternatively, the seam 22 can be formed by adhesively bonding the two pieces of fabric 14 together with a suitable adhesive such as Spray Trim Adhesive 08074, available from Minnesota Mining and Manufacturing Company, St. Paul, Minn.

The remaining elements of the orthopedic casting article 10 and the method by which an orthopedic cast 23 can be formed from the orthopedic casting article 10 will next be described with reference to FIG. 1 and FIG. 4. Referring first to FIG. 1, the article 10 is shown to have an anatomically related, predetermined shape, including a through aperture 24 providing a thumb hole that is adjacent and spaced apart from one end of a generally straight length portion 25 of the edge surface 20. The aperture 24 can be made by punching or cutting out a portion of the article 10 or, if a more finished periphery is desired, the layers of fabric 14 can be seamed together in a manner similar to that of seam 22 of FIG. 2.

The cast 23 of FIG. 4 is preferably formed by first activating the resin with water as taught by the patents referred to earlier. Next, a left or a right hand thumb is passed through the aperture 24. The generally straight edge surface portion 25 of the article 10 and the machine or chain stitch direction of the preferred fabric 14 are longitudinally aligned with the forearm, and the article 10 is circumferentially stretched around the forearm, stretchingly bringing together laterally disposed portions of the blank 10 into sealing relationship. The blank 10 is sufficiently dimensioned in a direction generally longitudinally aligned with the forearm to extend the length of the forearm to be covered by the cast 23, and the blank 10 is sufficiently dimensioned in a direction generally perpendicular to this longitudinal direction to at least circumferentially envelop the forearm and to conform to the forearm. The blank is preferably closed upon itself to form the cast 23 as will be detailed below.

The article 10 is preferably held in place while the resin is curing by the aid of restraining means 26. Such means 26 can include metal clips commonly used with conventional stretch bandages. Preferably, restraining means 26 comprises radiolucent clips. A right arm is shown in FIG. 4, but the casting article 10 can be equally well applied to a left arm.

By preferably stretchingly closing the article 10 upon itself and thereby bringing laterally disposed portions of the blank 10 together, the composite formed by the foam 12 and the fabric 14 is overlapped on itself betwen first and second lateral free edges of the blank, and the resultant cast 23 is provided with two thicknesses of the article 10 on the inside of the forearm. This double thickness can serve as extra reinforcement and act as a splint within the cast 23. Hence, the orthopedic casting article 10 of the present invention can provide the advantages of both a cast and a splint within an integral, comformable, orthopedic casting material. A further advantage of this built-in splint is that the resultant cast 23 places this reinforcement in the area or areas requiring the greatest support and/or strength; i.e., the reinforcement overlies the wrist and the palm of the hand. Conventional tape-wound casts, by way of contrast, cannot duplicate this advantage without additional time, layers and/or skillful application.

Closure of the article 10 is further preferably aided by projection means of the article 10 comprising a hand projection 28 and an arm projection 30. These two projecting portions 28 and 30 are positioned and dimensioned to insure the proper positioning of the resultant cast and greatly reduce or virtually eliminate any puckering of the article 10 that might otherwise occur when the article 10 is stretched around the forearm. The projecting portions 28 and 30 reduce puckering by reducing the pull on the article 10, which would otherwise result when the article 10 is stretched.

The two projecting portions 28 and 30 are defined by one of the lateral free edges of the blank 10 having a curvilinear shape. This curvilinearly-shaped free edge of the blank 10 is preferably defined by the generally curved edge surface portion 34 of the foam member 12 which in common with an edge of the fabric 14 as already described. This curvilinearly-shaped free edge of the blank 10 is generally opposite a second lateral free edge of the blank 10 having a linear shape. This linearly-shaped free edge of the blank 10 is preferably defined by the generally straight edge surface portion 25 of the foam member 12 which is in common with another edge of the fabric 14 as already described.

Before actually applying the article 10 to the forearm, a conventional, tubular, casting stockinet can be pulled over the forearm and cast padding applied as is well known in the art. Preferably to provide a total casting system which minimizes the total time required for cast application and takes full advantage of the quickness with which the cast of the instant invention can be applied, a tubular padding material such as one side lofted tubular fabric, made on an athletic sock machine available from Broadway Knitting Mills, 2152 Sacramento Street, Los Angeles, Calif. 90021, is pulled over the forearm before actually applying the article 10.

The article 10 can be easily adjusted or repositioned during curing but prior to setting of the resin without wrinkling. Further, the cast 23 can be removed from the arm by conventional techniques. The removal has been found to be easier and quieter, using conventional powered cast saws, than that achieved with the products of the prior art. Further, this removal has been found to be attended by less heat resulting from the action of the cast saw blade which, in turn, means less discomfort for the patient.

A lower leg embodiment of the present invention is shown in partially fabricated, plan view in FIG. 5 with portions broken away. A lower leg orthopedic casting article 50 is generally comprised of a unitary blank of a pliant, extensible layer or sheet of foam member 52 which is preferably at least partially open-celled and preferably backed on both sides by a knitted, extensible fabric 54 and impregnated with the moisture-curable resins described earlier. The foam member 52 and the fabric 54 are preferably the same as that described with reference to the casting article 10 of FIGS. 1–4, except that the fabric 54 is preferably 3/16 inch (0.476 cm), rather than ⅛ inch (0.317 cm), thick. The foam member 52 and the fabric 54 are preferably bonded throughout their interface as described with reference to the casting article 10 of FIGS. 1–4.

Figure 6:
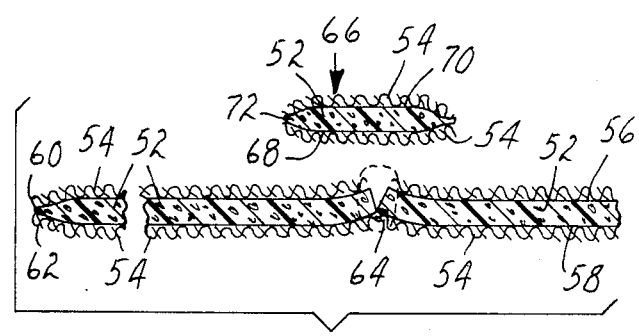
FIG. 6 is an enlarged cross-sectional view of the orthopedic casting article of FIG. 5 taken approximately along the line 6—6 of FIG. 5, with portions broken out and portions broken away, after the orthopedic casting article is fully fabricated.
Figure 7:
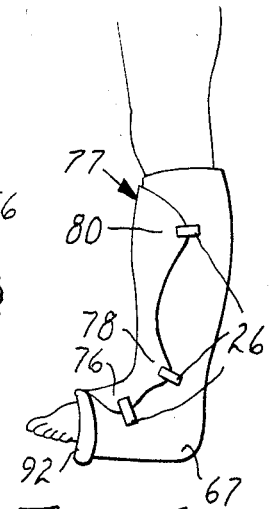
FIG. 7 is a plan view of the orthopedic casting article of FIG. 5 fully fabricated and formed into a lower leg cast.
Figure 8:
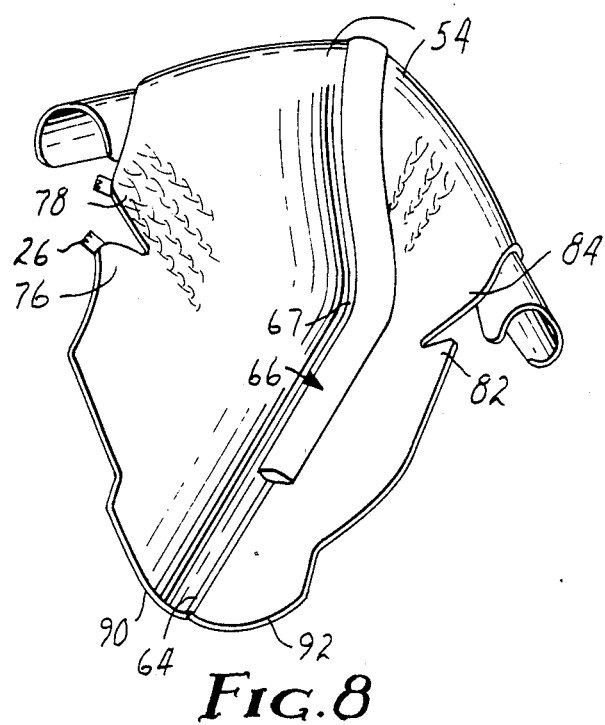
FIG. 8 is a fully fabricated, perspective view of the lower leg embodiment of FIG. 5 with portions rolled over to facilitate application.

Referring now to FIG. 6, together with FIG. 5, the orthopedic casting article 50 is shown, in an enlarged cross-sectional view taken approximately along the line 6—6 of FIG. 5 with portions broken away and after the article 50 is fully fabricated, to comprise the foam member 52 having two major, opposite side surfaces 56 and 58 and a peripherally extending interconnecting edge surface 60. The side surfaces 56 and 58 are covered by or faced with the fiberglass fabric 54. The fabric 54 preferably extends to the edge surface 60, which is similar to seam 22 of casting article 10 described earlier, to envelop and thereby hide or contain the foam member 52 within the fabric 54. The preferred article 50 further comprises a seam 64 preferably formed by stitching together two mirror-image edge portions 65 of the article 50 forming the parts to be positioned adjacent the calf muscle of the lower leg and the sole of the foot and defining a pocket 67, as shown in FIGS. 7 and 8. The pocket 67 is dimensioned to receive a heel as shown in FIG. 7.

Over the seam 64 is preferably attached a seam covering strip member 66 of the foam member 52 and the fabric 54. The foam member 52 of the strip member 66 has two major, opposite side surfaces 68 and 70 and an interconnecting edge surface 72. The side surfaces 68 and 70 are covered by the fiberglass fabric 54 as before. The side surface 68 of the strip member 66 is longitudinally aligned with and covers the seam 64 to provide the article 50 with a double thickness in the areas adjacent the back of the calf muscle of the lower leg, the heel of the foot and the sole of the foot. Preferably, the strip member 66 does not extend all the way to projections 90 and 92 to facilitate formation of a walking cast 77, as further described below.

The strip member 66 provides multiple functions. By covering the seam 64, the strip member 66 provides added comfort and strength to the portion of the article 50 that is ultimately disposed beneath the foot when the article is formed into the walking cast 77 as described below. By covering the seam 64, the foot is not exposed to the areas formed by the seam 64. Extending the strip member 66 nearly the length of the article 50, the strip member 66 provides extra strength to the ultimately formed walking cast 77 and can additionally serve as a splint within the cast 77 as described earlier with respect to the casting article 10 of FIGS. 1–4.

The strip member 66 can be attached to the remainder of the casting article 50 by a variety of conventional means, including stitching, adhesive bonding or heat or ultrasonic bonding. Alternatively, the double thickness provided by the strip member 66 and the heel pocket 67 can be provided by overlapping the edge portions 65 along their otherwise common lengths and conventionally affixing the edge portions 65 in this overlapped position.

The remaining elements of the orthopedic casting article 50 and the method by which the orthopedic cast 77 can be formed from the orthopedic casting article 50 will next be described with reference to FIGS. 5, 7 and 8. The cast 77 of FIG. 7 is preferably formed by first activating the resin with water as taught by the patents referred to earlier. Next, the leg is received within the article 50 adjacent the side surface 70 of the strip member 66, with the strip member 66 longitudinally aligned with the long axis of the leg and the heel within the pocket 67. The article 50 is circumferentially stretched around the leg to stretchingly bring together laterally disposed portions of the blank 50 into sealing relationship. The blank 50 is sufficiently dimensioned in a direction generally longitudinally aligned with the leg to extend the length of the leg to be covered by the cast 23, and the blank 50 is sufficiently dimensioned in a direction generally perpendicular to this longitudinal direction to at least circumferentially envelop the leg and to conform to the leg. The blank 50 is preferably closed upon itself to form the cast 77 as will be detailed below.

The article 50 is held in place while the resin is curing by the aid of restraining means 26, much as in the case of the article 10. The restraining means 26 preferably comprises the radiolucent clips as previously described. In the case of a left leg as shown in FIG. 7, the clips are positioned on the outside or the lateral side of the leg. In the case of a right leg, the clips are positioned on the inside or the medial side of the leg.

By stretchingly closing the article 50 upon itself and thereby bringing laterally disposed portions of the blank 50 together, the foam member 52 and the fabric 54 are overlapped between first and second lateral free edges of the blank, and the resultant cast 77 is provided with two thicknesses of the article 50 on the front or tibial area of the cast 77, generally opposite of the strip member 66. This double thickness provides extra-reinforcement or immobilization in the critical areas and can additionally serve as an internal splint within the cast 77 as described earlier in relation to the orthopedic casting article 10 of FIGS. 1–4. In this instance, the critical areas that are provided with additional support and/or strength are across the front or distal, anterior tibial region of the ankle from the overlap and around the heel strike area from the strip member 66. As with the casting article 10 of FIGS. 1–4, this is accomplished without additional time, layers and/or higher levels of skill associated with proper placement of tape products of the prior art.

Closure of the article 50 is further preferably aided by projection means of the article 50 comprising a foot projection 76, an ankle projection 78 and a shin projection 80. These projections are defined by one of the lateral free edges of the blank 50 having a curvilinear shape. These three projecting portions 76, 78 and 80 are positioned and dimensioned to insure the proper positioning of the resultant cast and greatly reduce or virtually eliminate any puckering of the article 10 as described in relation to their counterpart portions 28 and 30 of article 10 of FIGS. 1–4.

Generally opposite the projecting portions 76, 78 and 80, with respect to an axis 88, are three complimentary projecting portions 82, 84 and 86. These projections are defined by another of the lateral free edges of the blank 50 having a curvilinear shape. The portion 76 generally overlaps the portion 82 when the article 50 is closed upon itself. This is true both in the case of a left and a right leg. Similarly, the portion 78 generally overlaps the portion 84, and the portion 80 generally overlaps the portion 86 to properly position the cast 77 and to virtually eliminate any puckering as already described. With the preferred fabric as described above, the fabric 54 is preferably oriented with the weft direction 74 about 35 degrees from the axis 88, as shown in FIG. 5 to provide the best achievable fit of the article 50 around the lower leg, ankle and foot. The chain stitch direction 75 is shown to be perpendicular to the weft direction 74.

Before actually applying the article 50 to the leg, a conventional casting stockinette can be pulled over the leg and cast padding applied as is well known in the art. Preferably to provide a total casting system which minimizes the total time required for cast application and takes full advantage of the quickness with which the cast of the instant invention can be applied, a tubular padding material, such as one side lofted tubular fabric, made on an athletic sock machine available from Broadway Knitting Mills, 2152 Sacramento Street, Los Angeles, Calif. 90021, is pulled over the leg before actually applying the article 50.

Next, the leg portion of the article 50 is rolled over on itself as shown in FIG. 8 and water activated as before. The heel is generally received within the pocket 67. The rolled over portion of the article 50 is unrolled up the back of the leg with sufficient upward tension to maintain the heel within the pocket 67. The projection 80 is circumferentially overlapped the projection 86 and restrained generally over the shin. Next, the toe portion, formed of projections 90 and 92 by the seam 64, is pulled forward to firmly seat the heel within the pocket 67. The projections 78 and 84 are simultaneously stretched, sequentially overlapped and restrained as previously described. During this step, the projection 84 is manually held in place with the overlapping material. Similarly, the projections 76 and 82 are simultaneously stretched, sequentially overlapped and restrained as previously described. Next, the projections 80 and 86 are more tightly overlapped and restrained together into sealing relationship around the leg. Finally, the toe portion formed of projections 90 and 92 is folded back towards the heel as shown in FIG. 7 to accommodate different foot lengths, to provide additional strength, and to present a rounded surface to the toes and the sole of the foot. Additionally, the resultant cast 77 can be further molded in conventional fashion.

From the foregoing, it will be apparent that all of the objectives of this invention have been achieved by the casting article and method shown and described. It will also be apparent that various modifications and changes may be made by those skilled in the art without departing from the spirit of the invention as expressed in the accompanying claims. For example, a simple cylindrical cast article of the present invention may be used on the lower leg, the upper leg, the forearm, or the upper arm to support bone fractures by containment of the soft tissue around the bone without immobilizing adjacent joints. By a cylindrical cast article, it is meant that this article does not necessarily include a thumb hole or a heel pocket, or the other anatomically-related, predetermined shapes as described in conjunction with article 10 and 50, respectively. Similarly, such a simple cylindrical cast article of the present invention may be used to encompass the torso of a mammalian body and function as a body cast. Cylindrical cast articles of the present invention may also act as a casting brace where, for example, such cylinders on the upper and lower leg may be joined by a hinge at the knee. Such cylindrical cast articles provide all of the advantages previously described for the articles 10 and 50.

Because all of these modifications and changes may be made by one skilled in the art and without departing from the spirit of the invention as expressed in the accompanying claims, all matters shown and described are to be interpreted as illustrative and not in a limiting sense. The invention may be further illustrated by the following working examples which are merely illustrative and not intended to be limiting in any way.

EXAMPLE 1

The preferred embodiment of the short-leg walking cast article 50 of the present invention, as shown in FIGS. 5–8, was made as described below.

Lengths of foam-fabric composite were made by flame-bonding fiberglass knit fabric onto both opposing major surfaces of an open-celled polyurethane foam, by means of a two-pass process. The fiberglass fabric was the previously described 18 gauge, 2 bar, open chain, Raschel knit made with ECC 75 1/0 (electrical grade, continuous filaments, 0.000175 inch (0.000444 cm) diameter filaments, 7500 yards/lb. (6.85 Km/0.453 Kg), 1 strand) glass yarn. Using the previously described extensibility test method, the extensibility in the weft direction was 137.5% while extensibility in the machine or chain stitch direction was 37.5%. The polyurethane foam was 3/16 inch (0.476 cm) thick, type P-100, commercially available from Illbruck USA. Using the previously described extensibility test method, this foam-fabric composite exhibited 25% extensibility in the weft direction of the fabric and 12.5% extensibility in the chain stitch direction.

A sheet of the composite material of about 33 inches (83.8 cm) by 20 inches (50.8 cm) was cut from the roll length to accommodate patterns for the overlap side (including projections 76, 78 and 80), and the underlap side (including projections 82, 84 and 86), and the reinforcing strip member 66. The strip member 66 is preferably about 3 inches (7.62 cm) in width. The patterns were placed so that the long straight portion of the edge portions 65 to be seam-joined were at about 125 degrees to the direction of the chain stitch, which is about 35 degrees to the weft direction. The patterns were cut out and the edge portions 65 seamed together with an overedge type stitch, using a Brother model number MA4-B551 sewing machine, commercially available from Eastern Woolen Co., St. Paul, Minn., with a textured nylon thread. The seamed material was manually flattened, and the remaining edges tapered by applying heat and pressure through the use of a vertrod machine (model number 14P/PS purchased from Vertrod Corporation, USA). The strip member 66 with all the edge portions tapered as above was centered over the inner side of the seam 64 and extended the length of the seam 64 to within about 3 inches of the two projections 90 and 92. The strip member 66 was affixed by stitching with extensible thread.

The article 50 was coated with resin which had been made as follows: A 1 gallon, wide mouth jar equipped with a cover, a mechanical stirrer, an addition funnel, and a nitrogen supply, was charged with 2440.5 grams of Isonate® 143L obtained from Upjohn, LaPorte, Tex. At 5 minute intervals, the following were added with stirring: 3.7 grams of benzoyl chloride, 37.0 grams of 4-{2-[1-methyl-2-(4-morpholinyl)ethoxy]-ethyl}-morpholine prepared as described in copending, commonly assigned, U.S. application Ser. No. 784,344, filed Oct. 4, 1985, entitlet Catalysts for the Curing of a Water-Curable Isocyanate-Functional Prepolymer, in the name of Richard S. Buckanin, filed on even date herewith, 6.7 grams of Antifoaming Compound DB-100 from Dow Corning, Schiller Park, Ill., 17.8 grams of 2,6-Di-tert-butyl-4-methylphenol. Next, a mixture of NIAX Polyols PPG-425 (776.5 grams) and PPG-1025 (417.9 grams) from Union Carbide, Danbury, Conn. was added dropwise through the addition funnel. The resin was allowed to exotherm and was stirred for 1 hour after addition was complete. The jar was capped with an overlaying nitrogen layer. This resin was used in coating article 50 in an amount of about 70% by weight by spreading the resin on all surfaces of the article 50 and then manually kneading the resin into the foam-fabric composite material in a moisture-free chamber.

The strength of the resin loaded article 50 was predicted by the test method used to determine ring strength as described next below, which was predictive of the article's efficaciousness as a sufficiently strong, hard, rigid short-leg walking cast. Two inch (5.08 cm) diameter cylinders comprised of the resin loaded composite material in 1 and 2 layers were made as follows: Wearing protective gloves, the resin loaded composite material, pre-cut to 3 inch wide strips in lengths (parallel to the weft direction) for achieving 1 and 2 layer rings, were submerged in a bath of fresh water at a temperature of about 75 degrees Fahrenheit (24° C.) by laying the sample flat on its side in the water. The sample was removed from the water after 30 seconds, and the excess water was squeezed out to minimize dripping. The total time out of the water was approximately 10 seconds prior to winding the rings. One or two layers of the composite was uniformly wound around a 2 inch (5.08 cm) diameter aluminum mandrel with a crank handle and mounting bracket, rotating the handle away from the operator insuring that no single layer of sample extended beyond any other layer by more than 3/16 inch (0.476 cm). The excess sample was trimmed away, leaving approximately a 1 inch (2.54 centimeter) overlap, and the ring was gently smoothed and the overlapping edge held down until the resin had set. The ring was completely wound within 30 seconds after removal from the water. After the resin set, the ring was removed from the mandrel and allowed to cure for 24 hours at 75 degrees Fahrenheit (24° C.) and at a relative humidity of 55%. The cured ring was placed in a compression test fixture on an Instron Model 1122 with a 1000 pound (453.5 Kg) load cell, so that the overlap seam was not contacted by the penetrating bar of the compression test fixture. The compression test fixture was made with an upper and lower base. The lower base was attached to the Instron Tensil Tester, and the upper base was attached to the load cell. The lower base was equipped with two rectangular metal bars dimensioned to approximately ¾ inch (1.90 cm) wide, ½ inch (1.27 cm) thick, and 6 inches (15.2 cm) long, and attached 1½ inch (3.81 cm) apart to the metal base. The cured ring was placed on these bars and rested against the inside, rounded (⅛ inch (0.318 cm) radius) edges. The penetrating bar, approximately ¼ inch (0.635 cm) wide, ¾ inch (1.91 cm) thick, and 6 inches (15.2 cm) long was mounted to the upper base with a half round edge (⅛ inch (0.318 cm) radius) centered above and aligned parallel to the two bars on the lower base. The penetrating bar was lowered against the cured ring and the maximum load sustained by the ring was recorded. The ring strength of 1 layer was determined to be 35 pounds/inch (pounds per cylinder length in inches) (15.8 Kg/2.54 cm) and of 2 layers was 86 pounds/inch (38.9 Kg/2.54 cm).

While still in the moisture-free chamber, suitable polypropylene restraining clips were fastened onto the overlapping side projections 76, 78 and 80. The article 50 was sprayed on all surfaces with approximately 0.005 gram/square inch (0.005 gm/6.45 cm$^2$) of a mixture to reduce resin tackiness. This mixture was composed of a 12:12:76 w/w ratio of Brij ® 78, Brij ® 700 (ICI America, Inc., Atlas Chemical Div., Wilmington, Del. 19899), and Silicone Oil 200, viscosity 100 centistokes (Dow Corning, Schiller Park, Ill.). The article 50 was rolled-up and sealed in an airtight pouch, until ready for use by the applier.

The article 50 was applied to a human leg by first applying stockinet and overwrapping with a polyester cast padding. The article 50 was removed from the airtight pouch, dipped in water, and the excess water squeezed out. The article was applied as previously described. This application took about 45 seconds. The entire length of the short-leg walking cast was manually molded against the limb it enclosed and the resulting cast provided a snug fit, especially in the ankle area.

EXAMPLE 2

A foam-fabric composite material was prepared according to Example 1. A pattern as shown in FIG. 1 was cut out of an approximately 12 inch by 16 inch (30.5 cm×40.6 cm) piece of the composite material so that the straight edge surface portion 25 was parallel to the chain stitch (machine direction) of the composite fabric. The edges of article 10 of FIG. 1 including the entire periphery and the thumb hole 24 were tapered down, the tapered area extending approximately ½ inch (1.27 cm) in from the edge, using a Vertrod machine with the heat and dwell settings at 7.5. In a moisture-free chamber, the resin was applied to the surfaces of the article 10 according to Example 1 except that about 65% by weight of resin was used. Cast strength determined by the ring strength test as described in Example 1 was found to be 24 pounds/inch (10.87 Kg/2.54 cm) at one layer and 51 pounds/inch (23.01 Kg/2.54 cm) at two layers. The article 10 was sprayed on all surfaces with a resin-tack reducing formulation according to Example 1. Suitable polypropylene restraining clips were fastened on the projections 28 and 30. Article 10 was then rolled-up and sealed in an airtight pouch for storage until it was applied.

A stockinet was applied to a human arm up to the elbow and overwrapped with a polyester cast padding. The article 10 was removed from the airtight pouch, dipped in water, and the excess water was manually squeezed out. The article 10 was partially unrolled, exposing the thumb hole 24 and the edge surface 25. The article 10 was placed on the arm with the thumb through the hole 24 and the straight edge surface portion 25 aligned with the ulnar border of the arm. The projection 30 was then unrolled and stretched around the arm while holding the straight edge surface portion 25 in place for a snug fit and then secured in place with restraining clip. The projection 28 was then unrolled and stretched around the palm of the hand and through the web space while holding the underlapping straight edge surface portion 25 in place for a snug fit and then secured in place with the restraining clip. This application step took approximately 15 seconds. The resulting cast was then molded for the desired final conformation.

Within a few minutes the cast was set and provided a snug fit, especially in the wrist area.

What is claimed is:

1. An article suitable for forming an orthopedic cast around an animal body part comprising:
   a unitary blank having first and second lateral free edges, said blank being dimensioned in one direction sufficient to extend the length of said body part and dimensioned in a second direction sufficient to at least circumferentially envelop said body part, said blank comprising:
   (a) a pliant, extensible layer of an at least partially open-celled foam member,
   (b) an extensible fabric bonded to at least one major surface of said foam member, and
   (c) a curable resin impregnatably associated with said foam member of said blank whereby, upon activating said curable resin and stretchingly bringing laterally disposed portions of said blank together into sealing relationship around said body part, said orthopedic cast is provided.

2. The casting material according to claim 1 wherein said resin is comprised of a moisture-curable, isocyanate-functional, polyurethane prepolymer.

3. The casting article according to claim 2 wherein said resin further comprises a tack-reducing agent.

4. The casting article according to claim 1 further comprising means for restraining said blank around said body part.

5. The casting article according to claim 4 wherein said restraining means is radiolucent.

6. The casting article according to claim 1 wherein said extensible fabric is bonded to both major side surfaces of said foam member.

7. The casting article according to claim 6 wherein said fabric is comprised of a knitted fiberglass having an extensibility in one direction of at least 40%.

8. The casting article according to claim 7 wherein said blank has an extensibility in one direction of at least 12½%.

9. The casting article according to claim 1 wherein said foam member has in the range of 20–80 pores per linear centimeter.

10. The casting article according to claim 1 wherein said extensible fabric is a knitted fabric.

11. The casting article according to claim 1 wherein said blank is latitudinally dimensioned in said second direction to circumferentially extend, around said body part and provide an overlap region.

12. The casting article according to claim 11 wherein at least one of said first and second lateral free edges of said blank has a curvilinear shape defining projection means, said projection means being positioned and dimensioned to be formed around portions of said body part whereby said sealing relationship is substantially smooth and pucker free.

13. The casting material according to claim 12 wherein said other of said first and second lateral free edges of said blank has a linear shape and wherein said blank has a through aperture adjacent one end of said linearly-shaped edge, said aperture being dimensioned to receive a thumb.

14. The casting article according to claim 12 wherein said other of said first and second lateral free edges of said blank has a curvilinear shape defining second projection means, said projection means being positioned and dimensioned to be formed around portions of said body part, said second projection means being overlapped by said first projection means when said blank is circumferentially extended around said body part.

15. The casting article according to claim 14 further comprising a seam within said blank defining a toe portion and defining a pocket dimensioned to receive a heel.

16. The casting article according to claim 15 further comprising a seam covering member for covering said seam within said heel.

17. An orthopedic cast comprising:
   (a) a cast padding applied to an animal body part; and
   (b) a unitary blank according to claim 1 in sealing relationship around said body part with said resin cured to form said orthopedic cast.

18. The cast according to claim 17 wherein said cast padding is comprised of a tubular fabric.

19. An article suitable for forming an orthopedic cast around an animal body part comprising:
   a unitary blank having first and second lateral free edges, said blank being dimensioned in one direction sufficient to extend the length of said body part and dimensioned in a second direction sufficient to circumferentially extend around to envelop said body part and to provide an overlap region, said blank comprising:
   (a) a pliant, extensible layer of a foam member,
   (b) an extensible fabric bonded to at least one major surface of said foam member, and
   (c) a curable resin impregnatably associated with said blank whereby, upon activating said curable resin and stretchingly bringing laterally disposed portions of said blank together into sealing relationship around said body part, said orthopedic cast is provided, and
   wherein at least one of said first and second lateral free edges of said blank has a curvilinear shape defining projection means, said projection means being positioned and dimensioned to be formed around portions of said body part whereby said sealing relationship is substantially smooth and pucker free.

20. The casting material according to claim 19 wherein said resin is comprised of a moisture-curable, isocyanate-functional, polyurethane prepolymer.

21. The casting article according to claim 20 wherein said resin further comprises a tack-reducing agent.

22. The casting article according to claim 19 further comprising means for restraining said blank around said body part.

23. The casting article according to claim 22 wherein said restraining means is radiolucent.

24. The casting article according to claim 19 wherein said extensible fabric is bonded to both major side surfaces of said foam member.

25. The casting article according to claim 24 wherein said fabric is comprised of a knitted fiberglass having an extensibility in one direction of at least 40%.

26. The casting article according to claim 25 wherein said blank has an extensibility in one direction of at least 12½%.

27. The casting article according to claim 19 wherein said foam member has in the range of 20–80 pores per linear centimeter.

28. The casting article member according to claim 19 wherein said foam member is at least partially open-celled and wherein said curable resin is impregnating said foam member.

29. The casting article according to claim 19 wherein said extensible fabric is a knitted fabric.

30. The casting material according to claim 19 wherein said other of said first and second lateral free edges of said blank has a linear shape and wherein said blank has a through aperture adjacent one end of said linearly-shaped edge, said aperture being dimensioned to receive a thumb.

31. The casting article according to claim 19 wherein said other of said first and second lateral free edges of said blank has a curvilinear shape defining second projection means, said projection means being positioned and dimensioned to be formed around portions of said body part, said second projection means being overlapped by said first projection means when said blank is circumferentially extended around said body part.

32. The casting article according to claim 19 further comprising a seam within said blank defining a toe portion and defining a pocket dimensioned to receive a heel.

33. The casting article according to claim 32 further comprising a seam covering member for covering said seam within said heel.

34. A method for forming an orthopedic cast around an animal body part comprising the steps of:
  (a) providing a unitary blank according to claim 1;
  (b) activating said resin associated with said blank;
  (c) stretching said blank around said body part to conform said blank to said body part and form said orthopedic cast, and
  (d) overlapping said blank to provide a double thickness of said blank over a predetermined portion of said body part.

35. The method according to claim 34 further comprising the step of restraining said blank around said body part.

* * * * *